US011058446B2

(12) United States Patent
Gliner

(10) Patent No.: US 11,058,446 B2
(45) Date of Patent: Jul. 13, 2021

(54) ENT TOOL ANTENNA

(71) Applicant: Biosense Webster (Israel) Ltd., Yokneam (IL)

(72) Inventor: Vadim Gliner, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 621 days.

(21) Appl. No.: 15/676,579

(22) Filed: Aug. 14, 2017

(65) Prior Publication Data
US 2018/0070969 A1 Mar. 15, 2018

Related U.S. Application Data

(60) Provisional application No. 62/394,426, filed on Sep. 14, 2016.

(51) Int. Cl.
*A61B 17/24* (2006.01)
*A61M 1/00* (2006.01)
(Continued)

(52) U.S. Cl.
CPC .............. *A61B 17/24* (2013.01); *A61B 5/062* (2013.01); *A61B 18/1485* (2013.01);
(Continued)

(58) Field of Classification Search
CPC .. A61M 1/0025; A61M 1/008; A61M 1/0012; A61M 1/005; A61M 1/0052; A61M 1/0127; A61M 2025/0004; A61M 2025/0166; A61M 31/00; A61M 2205/0233; A61M 2205/0272;
(Continued)

(56) References Cited

U.S. PATENT DOCUMENTS

2006/0004323 A1 1/2006 Chang et al.
2007/0208252 A1 9/2007 Makower
(Continued)

FOREIGN PATENT DOCUMENTS

CN 202843784 4/2013

OTHER PUBLICATIONS

European Search Report dated Mar. 7, 2018 from corresponding European Patent Application No. 17190800.7.

*Primary Examiner* — Laura A Bouchelle
(74) *Attorney, Agent, or Firm* — Frost Brown Todd LLC

(57) ABSTRACT

An apparatus, including a handle and a first conductive tube that is attached to and extends from the handle. The first conductive tube is biocompatible, and a distal end of the first conductive tube is configured to be inserted into an orifice of a human being for a medical procedure. The apparatus includes a second conductive tube, that is attached to and is enclosed by the first conductive tube. The first and second conductive tubes together act as an antenna for electromagnetic radiation. An insulated conductive coil is fashioned around and is fixed to the second conductive tube, and the coil generates a signal in response to a magnetic field traversing the coil. The apparatus also includes a transceiver that receives the signal from the insulated conductive coil, and in response generates a radiofrequency signal at a preset frequency and conveys the radiofrequency signal to the second conductive tube for radiation therefrom as electromagnetic energy at the preset frequency.

19 Claims, 5 Drawing Sheets

(51) Int. Cl.
*A61B 5/06* (2006.01)
*A61B 18/14* (2006.01)
*A61B 34/20* (2016.01)
*A61B 18/00* (2006.01)
*A61B 5/00* (2006.01)
*A61B 17/00* (2006.01)
*A61B 18/12* (2006.01)
*A61B 90/00* (2016.01)

(52) U.S. Cl.
CPC ............ *A61B 34/20* (2016.02); *A61M 1/008* (2013.01); *A61B 5/066* (2013.01); *A61B 5/6847* (2013.01); *A61B 2017/00221* (2013.01); *A61B 2018/0091* (2013.01); *A61B 2018/00327* (2013.01); *A61B 2018/00577* (2013.01); *A61B 2018/00601* (2013.01); *A61B 2018/1226* (2013.01); *A61B 2034/2048* (2016.02); *A61B 2034/2051* (2016.02); *A61B 2034/2068* (2016.02); *A61B 2034/2072* (2016.02); *A61B 2090/374* (2016.02); *A61B 2090/376* (2016.02); *A61B 2090/3762* (2016.02); *A61M 2205/3592* (2013.01); *A61M 2205/52* (2013.01); *A61M 2205/8212* (2013.01); *A61M 2210/0681* (2013.01)

(58) Field of Classification Search
CPC ...... A61M 2205/051; A61M 2205/054; A61M 2205/057; A61M 2205/3317; A61M 2205/3515; A61M 2205/3523; A61M 2205/3576; A61M 2205/3592; A61M 2205/368; A61M 2210/0618; A61M 2210/0662; A61M 2210/0668; A61M 2210/0675; A61M 2210/0681; A61M 2210/1028; A61M 2210/1032; A61M 2210/1046; A61M 2210/105; A61B 1/00158; A61B 1/227; A61B 1/233; A61B 1/267; A61B 1/273; A61B 1/2733; A61B 2017/00039; A61B 2017/00221; A61B 2017/00787; A61B 2017/00876; A61B 17/24; A61B 2018/00071; A61B 2018/00077; A61B 2018/00083; A61B 2018/00327; A61B 2018/00488; A61B 2018/00636; A61B 2018/00642; A61B 18/18; A61B 2034/2051; A61B 5/062; A61B 2562/0223

See application file for complete search history.

(56) References Cited

U.S. PATENT DOCUMENTS

| | | | |
|---|---|---|---|
| 2011/0130750 A1* | 6/2011 | Ormsby | A61B 18/1815 606/33 |
| 2013/0345549 A1* | 12/2013 | Govari | A61B 5/6852 600/424 |
| 2016/0007842 A1 | 1/2016 | Govari et al. | |
| 2016/0008083 A1* | 1/2016 | Kesten | A61B 5/6851 600/424 |

* cited by examiner

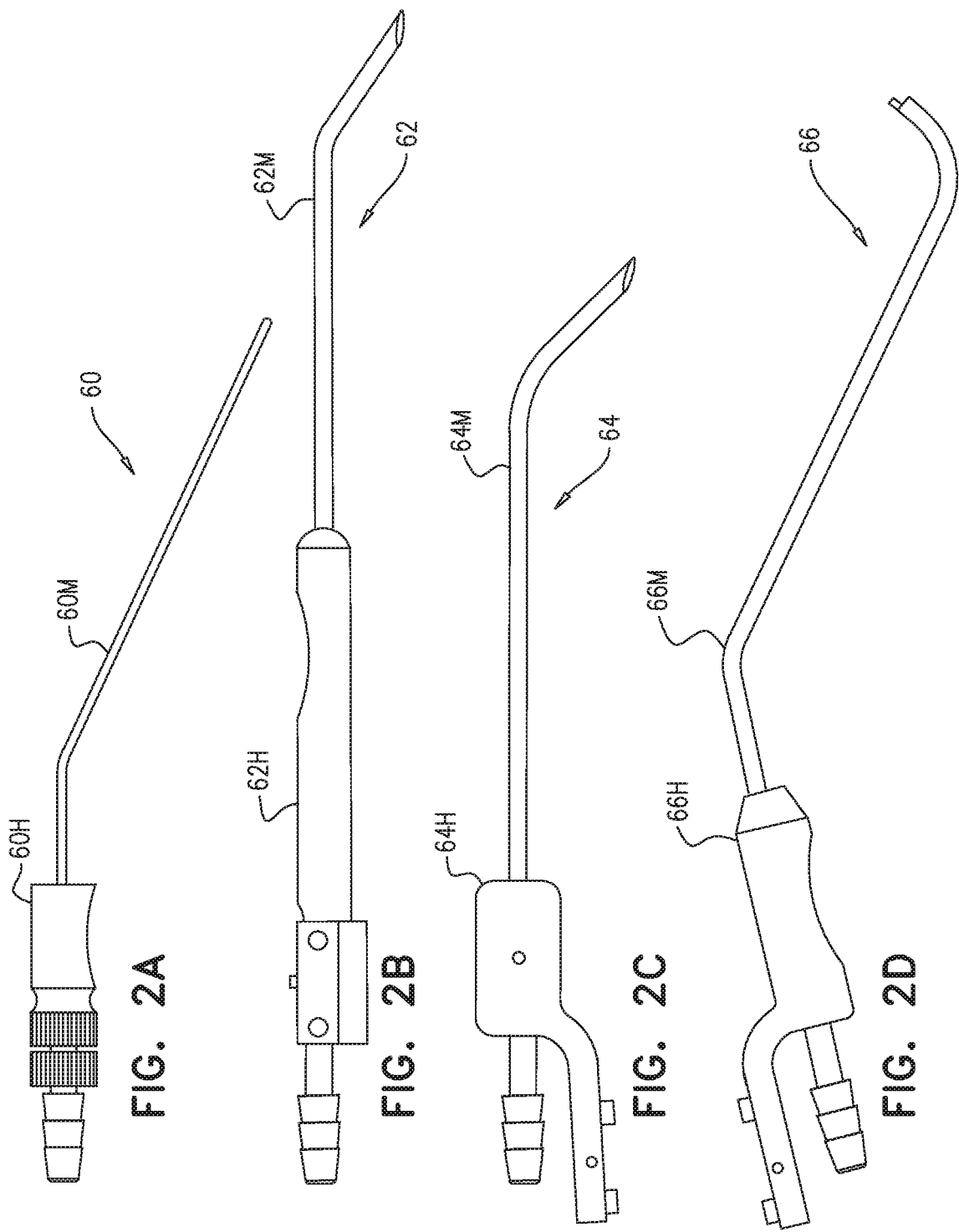

ENT TOOL ANTENNA

CROSS-REFERENCE TO RELATED APPLICATION

This application claims the benefit of U.S. Provisional Patent Application 62/394,426, filed Sep. 14, 2016, which is incorporated herein by reference.

FIELD OF THE INVENTION

This invention relates generally to surgical tools, and specifically to a rigid surgical tool which is coupled wirelessly to a system controller.

BACKGROUND OF THE INVENTION

Some surgical tools are stand-alone elements, not requiring additional connections such as cabling. However, "smart" tools, which measure parameters such as force exerted by the tool or the location and orientation of the tool, typically do require a connection to a system controller recording the parameters. While the connection may comprise cabling, the cabling may interfere with a physician's operation of the tool, so that a wireless connection may be preferable. Another advantage of wireless connectivity is that there is substantially no limit to the number of wireless tools that may be deployed, whereas cable connections require connectors, thus limiting the number of non-wireless tools.

Wireless connections require an antenna to transmit and receive their electromagnetic energy, and an efficient antenna may be relatively large compared to the size of the tool, and especially compared to the size of the handle of such a tool.

SUMMARY OF THE INVENTION

An embodiment of the present invention provides apparatus, including:

a handle a first conductive tube, fixedly attached to and extending from the handle, that is biocompatible, wherein a distal end of the first conductive tube is configured to be inserted into an orifice of a human being so as to perform a medical procedure therein;

a second conductive tube, fixedly attached to and enclosed by the first conductive tube, and acting, together with the first conductive tube, as an antenna for electromagnetic radiation;

an insulated conductive coil, fashioned around and fixed to the second conductive tube, that generates a signal in response to a magnetic field traversing the coil; and a transceiver connected to receive the signal from the insulated conductive coil, so as in response to generate a radiofrequency signal at a preset frequency and convey the radiofrequency signal to the second conductive tube for radiation therefrom as electromagnetic energy at the preset frequency.

In a disclosed embodiment the first conductive tube has a first electrical conductivity, and the second conductive tube has a second electrical conductivity greater than the first electrical conductivity.

In a further disclosed embodiment the transceiver is fixedly installed within the handle.

In a yet further disclosed embodiment the antenna has an antenna impedance, and the apparatus further includes an impedance converter that is connected to the transceiver so as to receive the radiofrequency signal at a transceiver impedance and convert the radiofrequency signal to a converted radiofrequency signal at the antenna impedance, and the impedance converter is coupled to the second conductive tube so that the tube receives the converted radiofrequency signal and in response radiates the electromagnetic energy at the preset radiofrequency. Typically, the impedance converter is fixedly installed within the handle.

In an alternative embodiment the apparatus includes a magnetic radiator assembly that radiates the magnetic field traversing the insulated conductive coil, and a processor that receives the electromagnetic radiation from the antenna, and that analyzes the received radiation to determine a position of the insulated conductive coil with respect to the magnetic radiator assembly.

In a further alternative embodiment the apparatus includes circuitry which is configured to perform a Discrete Fourier Transform on the signal from the insulated conductive coil so as to generate a transformed signal, and the transceiver is connected to receive the transformed signal and to generate the radiofrequency signal in response to the transformed signal.

In a yet further alternative embodiment the orifice is a nostril of the human being, and the handle, the first conductive tube, the second conductive tube, the insulated conductive coil, and the transceiver are formed into an ear, nose, and throat (ENT) surgical tool that is inserted into the nostril.

There is further provided, according to an embodiment of the present invention a method, including:

providing a handle;

fixedly attaching a first conductive tube to the handle so that it extends therefrom, wherein the first conductive tube is biocompatible, and wherein a distal end of the first conductive tube is configured to be inserted into an orifice of a human being so as to perform a medical procedure therein;

fixedly attaching a second conductive tube to the first conductive tube so that the first conductive tube encloses the second conductive tube, and wherein the second conductive tube acts, together with the first conductive tube, as an antenna for electromagnetic radiation;

fashioning an insulated conductive coil around the second conductive tube and fixing the coil to the second conductive tube, wherein the coil generates a signal in response to a magnetic field traversing the coil; and connecting a transceiver to receive the signal from the insulated conductive coil, so as in response to generate a radiofrequency signal at a preset frequency and convey the radiofrequency signal to the second conductive tube for radiation therefrom as electromagnetic energy at the preset frequency.

The present disclosure will be more fully understood from the following detailed description of the embodiments thereof, taken together with the drawings, in which:

BRIEF DESCRIPTION OF THE DRAWINGS

FIGS. 2A, 2B, 2C, and 2D are schematic diagrams of alternative ENT wireless tools that may be used in the system of FIG. 1, according to an embodiment of the present invention;

DETAILED DESCRIPTION OF EMBODIMENTS

Overview

Embodiments of the present invention overcome the problem of requiring a relatively large antenna for an ENT wireless tool by having the "business end" of the tool, typically a rod, act both to perform its surgical function and as an antenna for radiofrequency radiation transmitted from, and received by, the tool. By implementing the rod as an antenna, the handle of the tool may be made diminutive and delicate, as is preferred by many ENT physicians.

In one embodiment a wireless surgical tool, configured for an ENT procedure comprising suction from a sinus of a patient, comprises a handle to which is fixedly attached a biocompatible conductive tube. The tube extends from the handle, and is configured to be inserted into an orifice of the patient, typically a nostril, for the ENT procedure.

A second conductive tube is fixed within the biocompatible conductive tube, so that the second tube is enclosed by the biocompatible conductive tube. The two tubes together act as an antenna for electromagnetic radiation.

An insulated conductive coil is fashioned around, typically by winding, the second conductive tube so that it is fixed to the second conductive tube. The coil generates a signal in response to a magnetic field traversing the coil.

The wireless surgical tool also comprises a transceiver, which is typically located within the handle. The transceiver receives the signal from the insulated conductive coil, and in response generates a radiofrequency signal at a preset frequency, typically 2.4 GHz, and conveys the radiofrequency signal to the second conductive tube for radiation therefrom as electromagnetic energy at the preset frequency.

DETAILED DESCRIPTION

Figure 1:
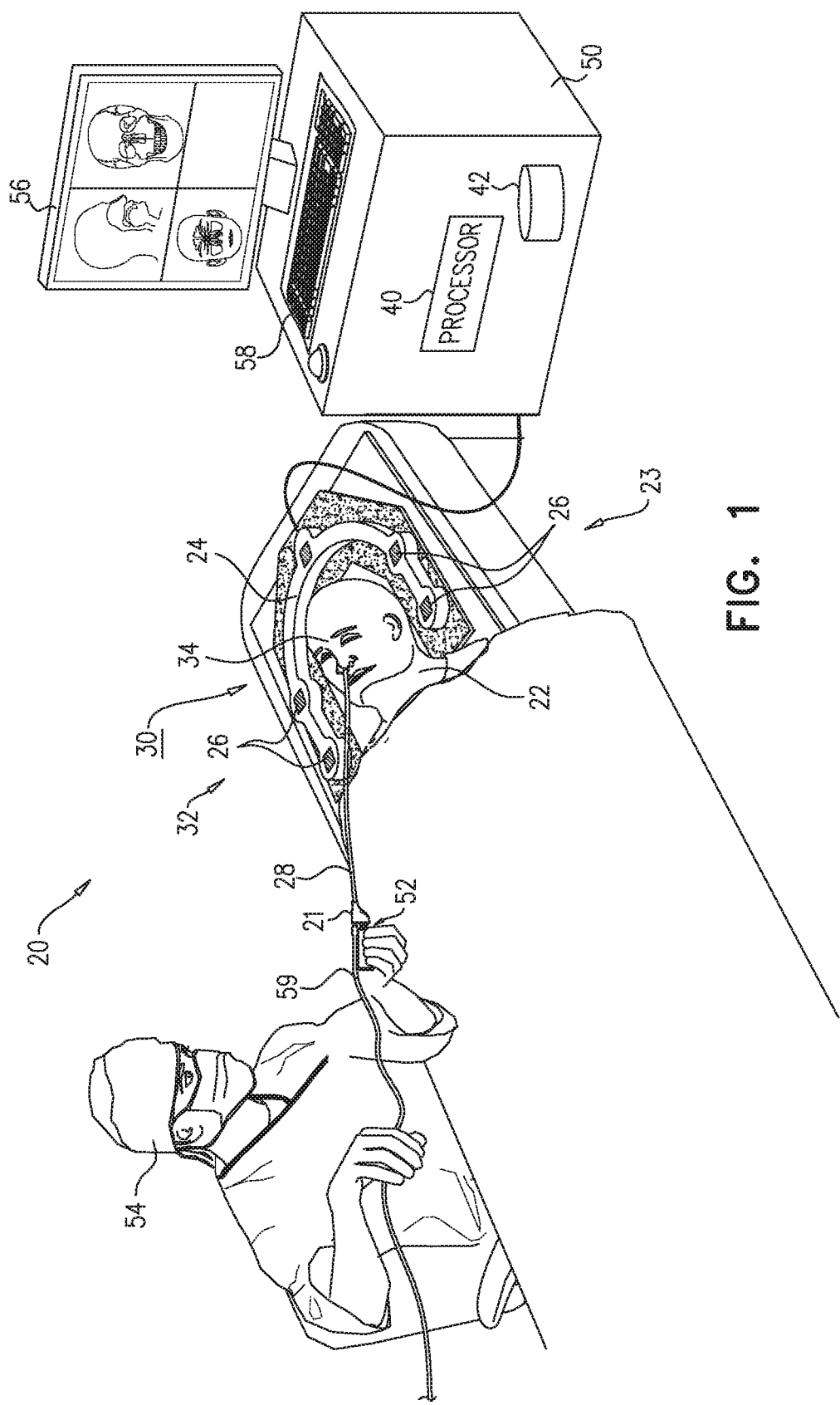
FIG. 1 is a schematic illustration of an ENT (ear, nose, and throat) system using an ENT wireless tool, according to an embodiment of the present invention.

Reference is now made to FIG. 1, which is a schematic illustration of an ENT (ear, nose, and throat) system 20, according to an embodiment of the present invention. As is described in more detail below, a wireless surgical tool 21 used in system 20 communicates wirelessly with a system processor 40, comprising a processing unit communicating with one or more memories, which operates the system. In the following description system 20 is assumed to be used to perform a medical procedure, comprising a nasal sinus procedure on a patient 22, and, as is described in more detail below, tool 21 comprises one or more magnetic sensors 32 that are tracked during the procedure by a magnetic tracking system 23. For the tracking to be effective, in system 20 frames of reference of a CT (computerized tomography) image of patient 22 and of magnetic tracking system 23, are registered. While the CT image may typically comprise a magnetic resonance imaging (MRI) image or a fluoroscopic image, in the description herein the image is assumed to comprise, by way of example, a fluoroscopic CT image, Prior to and during the sinus procedure, a magnetic radiator assembly 24, comprised in the magnetic tracking system, is positioned beneath the patient's head. Assembly 24 comprises magnetic field radiators 26 which are fixed in position and which transmit alternating sinusoidal magnetic fields into a region 30 wherein the head of patient 22 is located. By way of example, radiators 26 of assembly 24 are arranged in an approximately horseshoe shape around the head of patient 22. However, alternate configurations for the radiators of assembly 24 will be apparent to those having ordinary skill in the art, and all such configurations are assumed to be comprised within the scope of the present invention.

In some embodiments, prior to the procedure, for the registration performed by system 20, a distal tip of tool 21, having a magnetic sensor 32 at the tip, is touched at different regions of the skin of patient 22. The signals induced in the sensor in response to its interaction with the magnetic fields produced by assembly 24 enable the position of the tip to be tracked, once assembly 24 has been calibrated. A probe handle 52, held by a physician 54 operating system 20, is connected to the proximal end of tool 21, the handle allowing the physician to manipulate the tool. Flexible tubing 59 connects to handle 52, the tubing permitting the medical procedure referred to above, comprising drainage of fluid through a lumen of tool 21. In some embodiments handle 52 may incorporate controls allowing the physician to control acquisition of the signals from the distal tip sensor, when the distal tip touches the skin. The Carto® system produced by Biosense Webster, of Diamond Bar, Calif., uses a system similar to that described herein for finding the location and orientation of a coil in a region irradiated by magnetic fields. Alternatively, one or more other methods for registration, known in the art, may be used to perform the registration.

Elements of system 20, including radiators 26, are controlled by system processor 40. Processor 40 may be mounted in a console 50, which comprises operating controls 58 that typically include a keypad and/or a pointing device such as a mouse or trackball. Console 50 connects to the radiators via a cable and/or wirelessly. Physician 54 uses operating controls 58 to interact with the processor while performing the ENT procedure using system 20. While performing the procedure, the processor may present results of the procedure on a screen 56.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 uses the software, inter alia, to operate magnetic radiators 26 of assembly 24. As stated above the radiators transmit sinusoidal alternating magnetic fields of different frequencies into region 30, including the head of patient 22, and the fields from the radiators induce signals in sensors 32. As is described below, the signals, and/or data derived from the signals, may be transmitted wirelessly to the processor which analyzes the received data and/or signals to derive location and orientation values, measured with respect to a frame of reference defined by the assembly, for the sensors.

FIGS. 2A, 2B, 2C, and 2D are schematic diagrams of ENT wireless tools, alternative to tool 21, that may be used in system 20, according to an embodiment of the present invention. FIG. 2A illustrates an ENT tool 60, having a handle 60H fixedly connected to an inflexible tubular member 60M; FIG. 2B illustrates an ENT tool 62, having a handle 62H fixedly connected to an inflexible tubular member 62M; FIG. 2C illustrates an ENT tool 64, having a handle 64H fixedly connected to an inflexible tubular member 64M; and FIG. 2D illustrates an ENT tool 66, having a handle 66H fixedly connected to an inflexible tubular member 66M. Tools 60, 62, 64, and 66 are generally similar in shape to tool 21, all the tools having a handle fixedly connected to a tubular member. Tool 21 is described in more detail below, with reference to FIGS. 3A and 3B.

Figure 3A:
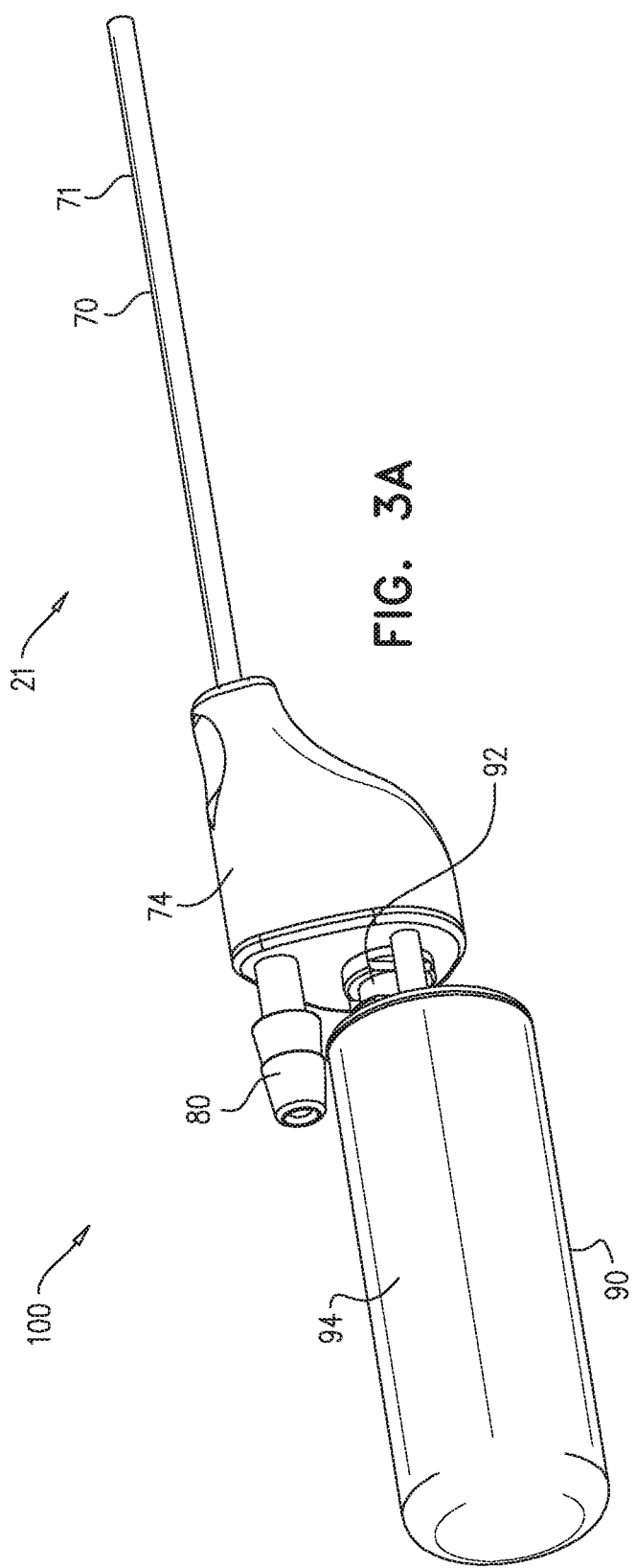
FIG. 3A and FIG. 3B are respectively schematic diagrams of the exterior and interior of the wireless tool used in the system of FIG. 1, according to an embodiment of the present invention.
Figure 3B:
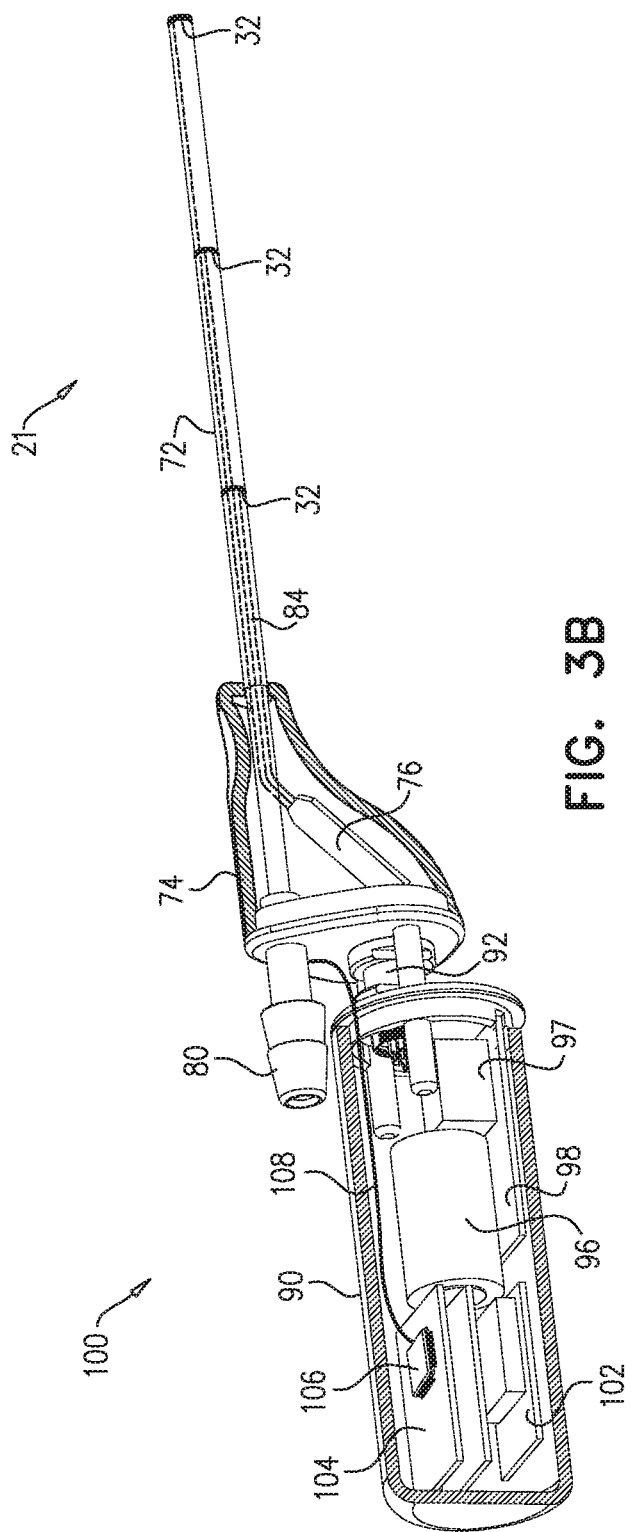

FIG. 3A and FIG. 3B are respectively schematic diagrams of the exterior and interior of ENT wireless tool 21, according to an embodiment of the present invention. As shown in FIG. 3A a distal end of tool 21 comprises an external inflexible biocompatible metallic tube 70, typically formed from a poor electrical conductor such as titanium alloy or stainless steel. Tube acts as a protective shield that is fixed to an internal inflexible metallic tube 72 (FIG. 3B, where tube 70 has been hidden), which is typically a good electrical conductor such as copper. As is described further below, tube 72 together with tube 70 form a tubular member that acts as an antenna 71 of tool 21, so that antenna 71 is also referred to herein as tubular member 71. In the medical procedure described herein, member 71 may be inserted into an orifice of patient 22, such as a nostril of the patient.

Tube 70 is fixedly attached to a casing 74 (part of which is shown as transparent in FIG. 3B) which encloses a printed circuit board (PCB) 76. A tubular fluid connection 80 is also fixedly attached to casing 74, and, as shown in FIG. 3B, internal tube 72 couples to connection 80. Connection 80 connects to tubing 59 (FIG. 1) and is sealed to tube 72, so that during the ENT procedure body fluids may drain through internal tube 72 and connection 80 without leaking into casing 74.

Sensors 32, in the form of insulated coils of wire, are fashioned around tube 72, so that in the following description sensors 32 are also referred to herein as coils 32. By way of example, tool 21 is assumed to have three generally similar coils 32, one at the distal tip of tube 72, and two at more proximal locations on the tube. However, other embodiments of the present invention may have more or less than three coils 32. Each coil 32 is connected by a pair of insulated conductors 84 to PCB which comprises low noise pre-amplifiers and an analog-to-digital (A/D) converter.

A wireless sub-assembly 90 fixedly connects, via a water sealed connector 92, to casing 74. Connector 92 is water sealed so that subsequent sterilization of tool 21 does not adversely affect components of tool 21. Sub-assembly 90 is enclosed by a protective casing 94, which physician 54 is also able to use as handle 52, so that casing 94 is also referred to herein as handle 52.

In embodiments of the present invention the handle is typically configured to be as small as possible, and is also configured to be firmly grasped by the physician performing the procedure. As described below handle 52 contains a battery, and the size of the battery typically limits how small the handle can be made. In one embodiment handle 52 has a cylindrical shape, with an approximate diameter of 2 cm and an approximate length of 3 cm.

Connector 92 has a plurality of conductors which transfer power to PCB 76, and which transfer clocking and data signals between the PCB and other circuitry 100 (described below) within sub-assembly 90. The power and clocking signals are derived from power and clocking circuitry 98 (which is typically a PCB) which is driven by a battery 96. Circuitry 98 also provides power and clocking signals to other elements of sub-assembly 90. In some embodiments sub-assembly 90 also incorporates an accelerometer 97, which may be configured to turn off the power from battery 96 when tool 21 is not in use.

A signal processing board 102, comprising a field programmable gated array (FPGA) coupled to a processor, receives the digital signals from the A/D converter of PCB 76. In one embodiment board 102 is formed from an FPGA module produced by Enclustra of Zurich, Switzerland. The processor analyzes the signals to find the magnitudes of the magnetic fields traversing sensors 32, and the magnitudes are transferred to a transceiver board 104.

Transceiver board 104 is configured to transmit and receive at predetermined radiofrequencies, which, by way of example, are assumed to be in the 2.4 GHz band. In one embodiment transceiver board 104 is formed from a CC2543 System-on-Chip produced by Texas Instruments of Dallas, Tex. Board 104 encodes the data received into its transmitting frequency, in preparation for wireless transmission to system processor 40.

Board 104 is coupled to antenna 71 by a balun 106 and a cable 108, the cable being galvanically connected to tube 72. The balun acts as an impedance converter, so as to match the impedance of board 104 with the impedance of cable 108. Cable 108 is typically coaxial, with an impedance of 50Ω. The balun also inherently acts as a filter for the 2.4 GHz band. In one embodiment balun 106 comprises a 2450BM15 balun produced by Johanson Technology Inc. of Camarillo Calif.

As is known in the art, components that operate at frequencies of the order of 2.4 GHz typically operate according to a distributed element model, having capacitive, inductive, and resistive properties. This contrasts with the operation of components at lower frequencies, which typically operate according to a lumped element model, having either capacitive or inductive or resistive properties. Thus, components of tool 21 prior to transceiver board 104 may typically be considered as lumped components, while components of the board, and subsequent components such as cable 108 and antenna 71, typically operate in a distributed fashion.

As stated above, tubes 70 and 72 act as antenna 71, and in embodiments of the present invention the antenna receives from board 104, and transmits to the board, radiofrequency signals at the predetermined radiofrequencies of board 104. In operation, antenna 71 transmits electromagnetic radiation from the antenna, and receives electromagnetic radiation at the antenna.

From a theoretical point of view, antenna 71 may be considered to operate as a monopole antenna, being resonant at any odd number of quarter wavelengths. Thus, for the 2.4 GHz band having a wavelength of approximately 0.125 m, antenna 71, i.e., tubes 70 and 72, may be formed to be any odd number of approximately 3 cm lengths. In practice, because of the distributed properties of tubular member 71 and coaxial cable 108, actual values of the length of the tubular member may differ from the theoretical values.

In one embodiment antenna 71 is formed to be approximately 15 cm long, and the inventors have found that using this length the antenna, i.e. tubular member 71, resonates with a relatively high Q. As will be understood, the Q is reduced because antenna 71 has an external tube 70 formed from material having a relatively poor electrical conductivity, and the diminution of Q makes selection of a resonant length of the antenna easier. Consequently, those having ordinary skill in the art will be able to select other lengths than 15 cm for antenna 71 without undue experimentation.

Furthermore, while the above explanation has been directed to use of an ENT wireless tool in the 2.4 GHz band, those having ordinary skill in the art will be able to adapt the description, mutatis mutandis, for ENT wireless tools operating in other bands, including, but not limited to, ultra high frequency (UHF) and super high frequency (SHF) bands.

Figure 4:
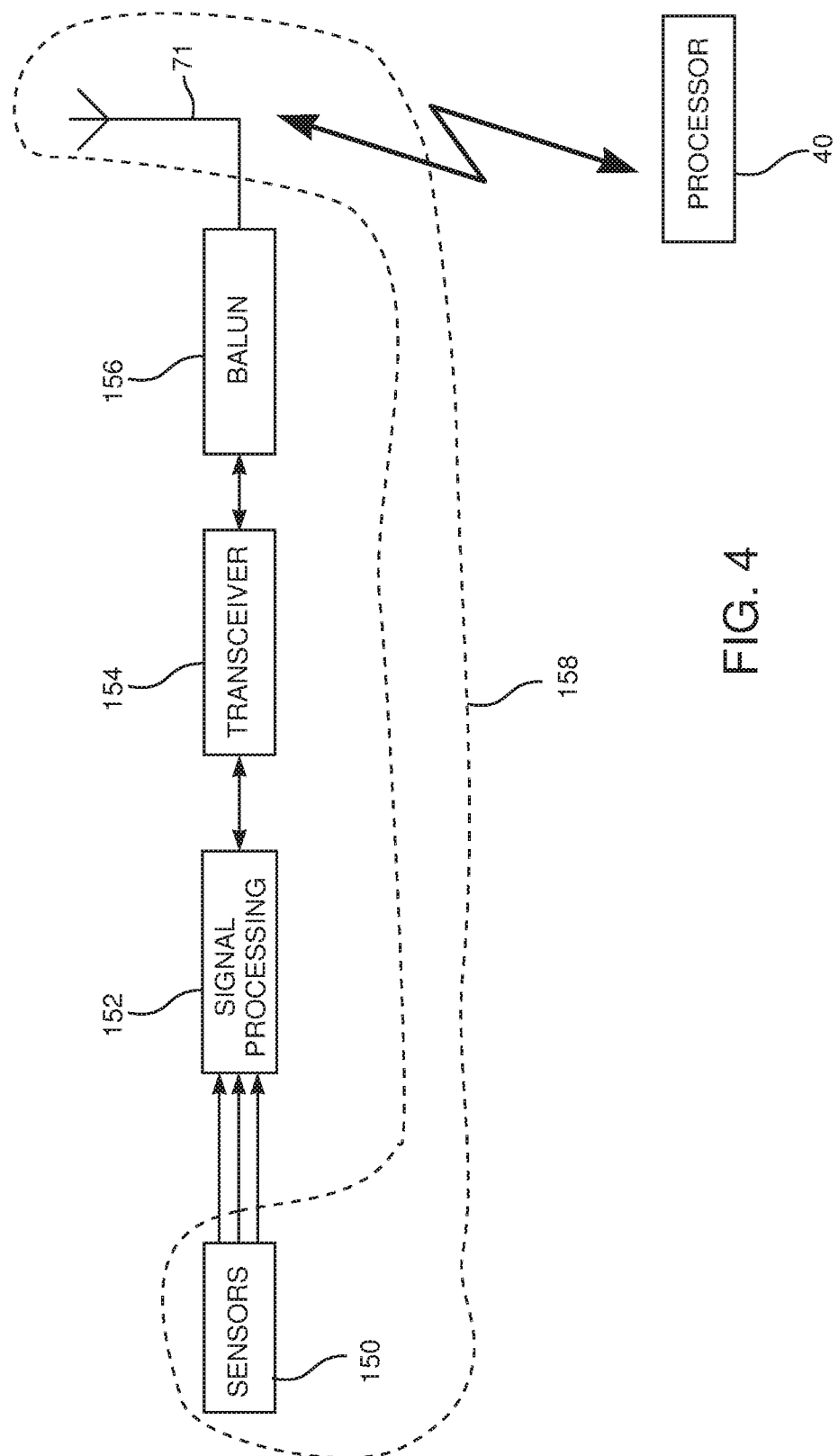
FIG. 4 is a block diagram of an ENT wireless tool, according to an embodiment of the present invention.

FIG. 4 is a schematic block diagram of an ENT wireless tool, according to an embodiment of the present invention. While, for clarity, the following explanation of the block diagram is directed to tool 21, it will be understood that the block diagram, mutatis mutandis, applies to other ENT wireless tools described herein. A sensors block 150 corresponds to sensors 32, the sensors being physically located on tube 72 of antenna 21. Signals from sensors block 150 are fed to a signal processing block 152, which comprises boards 76 and 102. Data from the signal processing block is fed to a transceiver block 154, corresponding to transceiver board 104, and encoded data from the board is fed, via a balun and filter block 156, comprising balun 106, to antenna 71. A broken line 158 signifies that sensors 32 and antenna 71 are physically at the same location, tube 72.

Antenna 71 radiates electromagnetic radiation, conveying the signals from sensors 32 and/or data derived from the signals, to processor 40. In one embodiment the data derived from the signals is converted in signal processing block 152, i.e., boards 76 and 102, using a Fourier Transform, typically a Discrete Fourier Transform (DFT), and the DFT is transmitted from antenna 71. Performing a DFT on the signals reduces the amount of data needed to be sent.

Typically, the electromagnetic radiation may also be used to convey other operating parameters of tool 21, such as a timestamp, a state of battery 96, and/or values derived from other elements that may be incorporated into the tool, for example, accelerometer 97, to the processor. Processor 40 may also be configured to convey, via electromagnetic radiation received by antenna 71, control signals from the processor for tool 21.

It will be understood that in embodiments of the present invention tube 72 has multiple functions: acting as an antenna for tool 21, retaining location tracking sensors for the tool, and performing the surgical functions of the tool.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
   (a) a handle;
   (b) a first conductive tube, fixedly attached to and extending from the handle, that is biocompatible, wherein a distal end of the first conductive tube is configured to be inserted into an orifice of a human being so as to perform a medical procedure therein;
   (c) a second conductive tube, fixedly attached to and enclosed by the first conductive tube, and configured to act, together with the first conductive tube, as an antenna for electromagnetic radiation;
   (d) an insulated conductive coil, fashioned around and fixed to the second conductive tube, that is configured to generate a signal in response to a magnetic field traversing the insulated conductive coil, the generated signal being indicative of a position of the insulated conductive coil relative to the magnetic field; and
   (e) a transceiver configured to receive the signal from the insulated conductive coil and to generate a radiofrequency signal at a preset frequency that is based upon the signal, the transceiver being further configured to convey the radiofrequency signal to the second conductive tube for wireless radiation therefrom as electromagnetic energy at the preset frequency to a processor of an instrument position tracking assembly.

2. The apparatus according to claim 1, wherein the first conductive tube has a first electrical conductivity, and the second conductive tube has a second electrical conductivity greater than the first electrical conductivity.

3. The apparatus according to claim 1, wherein the transceiver is fixedly installed within the handle.

4. The apparatus according to claim 1, wherein the antenna has an antenna impedance, the apparatus further comprising an impedance converter that is connected to the transceiver so as to receive the radiofrequency signal at a transceiver impedance and convert the radiofrequency signal to a converted radiofrequency signal at the antenna impedance, and wherein the impedance converter is coupled to the second conductive tube so that the second conductive tube receives the converted radiofrequency signal and in response radiates the electromagnetic energy at the preset frequency.

5. The apparatus according to claim 4, wherein the impedance converter is fixedly installed within the handle.

6. The apparatus according to claim 1, further comprising a magnetic radiator assembly that is configured to radiate the magnetic field traversing the insulated conductive coil, wherein the processor is configured to receive the electromagnetic radiation from the antenna and analyze the received electromagnetic radiation to determine the position of the insulated conductive coil with respect to the magnetic radiator assembly.

7. The apparatus according to claim 1, further comprising circuitry which is configured to perform a Discrete Fourier Transform on the signal from the insulated conductive coil so as to generate a transformed signal, and wherein the transceiver is connected to receive the transformed signal and to generate the radiofrequency signal in response to the transformed signal.

8. A method, comprising:
   (a) providing a handle;
   (b) fixedly attaching a first conductive tube to the handle so that the first conductive tube extends therefrom, wherein the first conductive tube is biocompatible, and wherein a distal end of the first conductive tube is configured to be inserted into an orifice of a human being so as to perform a medical procedure therein;
   (c) fixedly attaching a second conductive tube to the first conductive tube so that the first conductive tube encloses the second conductive tube, and wherein the second conductive tube acts, together with the first conductive tube, as an antenna for electromagnetic radiation;
   (d) fashioning an insulated conductive coil around the second conductive tube and fixing the insulated conductive coil to the second conductive tube, wherein the insulated conductive coil generates a signal in response to a magnetic field traversing the insulated conductive coil that is indicative of a position of the insulated conductive coil relative to the magnetic field; and
   (e) connecting a transceiver to receive the signal from the insulated conductive coil, so as in response to generate a radiofrequency signal at a preset frequency and convey the radiofrequency signal to the second conductive tube for radiation therefrom as electromagnetic energy at the preset frequency to a processor of an instrument position tracking assembly.

9. The method according to claim 8, wherein the first conductive tube has a first electrical conductivity, and the second conductive tube has a second electrical conductivity greater than the first electrical conductivity.

10. The method according to claim 8, wherein the transceiver is fixedly installed within the handle.

11. The method according to claim 8, wherein the antenna has an antenna impedance, the method further comprising providing an impedance converter that is connected to the transceiver so as to receive the radiofrequency signal at a transceiver impedance and convert the radiofrequency signal to a converted radiofrequency signal at the antenna impedance, and wherein the impedance converter is coupled to the second conductive tube so that the second conductive tube receives the converted radiofrequency signal and in response radiates the electromagnetic energy at the preset frequency.

12. The method according to claim 11, wherein the impedance converter is fixedly installed within the handle.

13. The method according to claim 8, further comprising a providing a magnetic radiator assembly that radiates the magnetic field traversing the insulated conductive coil, the method further comprising receiving the electromagnetic radiation from the antenna, and analyzing the received radiation to determine the position of the insulated conductive coil with respect to the magnetic radiator assembly.

14. The method according to claim 8, further comprising performing a Discrete Fourier Transform on the signal from the insulated conductive coil so as to generate a transformed signal, and wherein the transceiver is connected to receive the transformed signal and to generate the radiofrequency signal in response to the transformed signal.

15. The method according to claim 8, wherein the orifice comprises a nostril of the human being, and wherein the handle, the first conductive tube, the second conductive tube, the insulated conductive coil, and the transceiver are comprised in an ear, nose, and throat (ENT) surgical tool inserted into the nostril.

16. An apparatus, comprising:
(a) a handle;
(b) a first conductive tube extending from the handle, wherein a distal end of the first conductive tube is configured to be inserted into an ear, nose, or throat of a human being so as to perform a medical procedure in the ear, nose, or throat of the human being;
(c) a second conductive tube extending from the handle and enclosed by the first conductive tube, the first conductive tube and the second conductive tube being configured to act together as an antenna to wirelessly transmit data signals;
(d) an insulated conductive coil coupled with the second conductive tube and configured to sense a magnetic field traversing the insulated conductive coil, the insulated conductive coil being further configured to generate an output signal indicative of a position of the insulated conductive coil relative to the magnetic field; and
(e) a transceiver configured to receive the output signal from the insulated conductive coil and to generate a data signal that is based upon the output signal, wherein the transceiver is further configured to convey the data signal to the antenna for wireless radiation from the antenna to an instrument position tracking assembly.

17. The apparatus according to claim 16, wherein the transceiver is fixedly installed within the handle.

18. The apparatus according to claim 16, wherein the antenna has an antenna impedance, the apparatus further comprising an impedance converter that is connected to the transceiver so as to receive the data signal at a transceiver impedance and convert the data signal to a converted data signal at the antenna impedance, and wherein the impedance converter is coupled to the second conductive tube so that the second conductive tube receives the converted data signal and in response wirelessly radiates therefrom.

19. The apparatus according to claim 16, further comprising a magnetic radiator assembly that radiates the magnetic field traversing the insulated conductive coil, wherein the instrument position tracking assembly wirelessly receives the data signal from the antenna and analyzes the received data signal to determine the position of the insulated conductive coil with respect to the magnetic radiator assembly.

* * * * *